United States Patent
Eller et al.

[11] Patent Number: 5,739,405
[45] Date of Patent: Apr. 14, 1998

[54] PREPARATION OF AMINES FROM OLEFINS OVER ZEOLITES OF THE TYPE SSZ-37

[75] Inventors: Karsten Eller, Ludwigshafen; Rudolf Kummer, Frankenthal; Peter Stops, Altrip, all of Germany

[73] Assignee: BASF Aktiengesellschaft, Ludwigshafen, Germany

[21] Appl. No.: 760,296

[22] Filed: Dec. 4, 1996

[30] Foreign Application Priority Data

Dec. 8, 1995 [DE] Germany .................. 195 45 876.1

[51] Int. Cl.⁶ ................................... C07C 209/60
[52] U.S. Cl. .................. 564/485; 564/316; 564/373; 564/374; 564/381; 564/382; 564/391; 564/392; 564/408; 564/462
[58] Field of Search ................. 564/485, 316, 564/373, 374, 381, 382, 391, 392, 408, 462

[56] References Cited

U.S. PATENT DOCUMENTS

| | | | |
|---|---|---|---|
| 4,375,002 | 2/1983 | Peterson et al. | 564/445 |
| 4,536,602 | 8/1985 | Deeba | 564/485 |
| 5,254,514 | 10/1993 | Nakagawa | 502/62 |

FOREIGN PATENT DOCUMENTS

| | | | |
|---|---|---|---|
| 133 938 | 7/1884 | European Pat. Off. | |
| 132 736 | 7/1984 | European Pat. Off. | |
| 101 921 | 4/1986 | European Pat. Off. | |
| 0 305 564 | 3/1989 | European Pat. Off. | |
| 305 564 | 3/1989 | European Pat. Off. | |
| 431 451 | 11/1990 | European Pat. Off. | |
| 0 587 424 | 3/1994 | European Pat. Off. | 564/485 |
| 42 06 992 | 3/1992 | Germany . | |
| WO93/17995 | 9/1993 | WIPO . | |

OTHER PUBLICATIONS

Brunet et al., J. Mol. Catal., vol. 49 (1989), pp. 235–259.

*Primary Examiner*—Peter O'Sullivan
*Attorney, Agent, or Firm*—Keil & Weinkauf

[57] ABSTRACT

A process for the preparation of amines of the general formula I

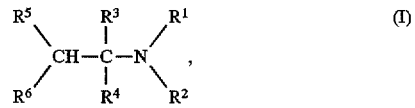

in which $R^1$, $R^2$, $R^3$, $R^4$, $R^5$, $R^6$ denote hydrogen, $C_1$–$C_{20}$ alkyl, $C_2$–$C_{20}$ alkenyl, $C_2$–$C_{20}$ alkynyl, $C_3$–$C_{20}$ cycloalkyl, $C_4$–$C_{20}$ alkylcycloalkyl, $C_4$–$C_{20}$ cycloalkylalkyl, aryl, $C_7$–$C_{20}$ alkylaryl, or $C_7$–$C_{20}$ aralkyl, $R^1$ and $R^2$ together denote a saturated or unsaturated $C_3$–$C_9$ alkylene dichain and $R^3$ or $R^5$ denotes $C_{21}$–$C_{200}$ alkyl, $C_{21}$–$C_{200}$ alkenyl or they together form a $C_2$–$C_{12}$ alkylene dichain, by the reaction of olefins of the general formula II

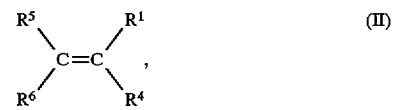

in which $R^3$, $R^4$, $R^5$, and $R^6$ have the above meanings, with ammonia or primary or secondary amines of the general formula III

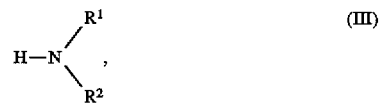

in which $R^1$ and $R^2$ have the above meanings, at temperatures ranging from 200° to 350° C. and pressures ranging from 100 to 300 bar in the presence of a heterogeneous catalyst, wherein the heterogeneous catalyst used is a zeolite of the type SSZ-37.

11 Claims, No Drawings

PREPARATION OF AMINES FROM OLEFINS OVER ZEOLITES OF THE TYPE SSZ-37

The present invention relates to a process for the preparation of amines by the reaction of ammonia or primary or secondary amines with olefins at elevated temperatures and pressures in the presence of zeolites of the type SSZ-37.

An overview of the methods of aminating olefins is given in "Functionalisation of Alkenes: Catalytic Amination of Monoolefins", J. J. Brunet et al J. Mol. Catal., 49 (1989), pp 235 to 259.

Basically there are two catalyst mechanisms. The olefin is coordinated via a metal complex. This activated species can be attacked by the nucleophilic amine and form a more highly aminated product. The amine can be chemisorbed at acid centers or metal centers (via metal amides) and caused, thus activated, to react with the olefin.

Well-suited catalysts are zeolites. They are distinguished by a large number of catalytically active centers, combined with a large surface area. The zeolites described differ in type and requisite post-treatment (eg thermal treatment, dealumination, acid treatment, metal ion exchange, etc). Examples thereof are described in U.S. Pat. No. 4,375,002, U.S. Pat. No. 4,536,602, EP-A 305,564, EP-A 101,921, DE-A 4,206,992.

EP-A 133,938, EP-A 431,451 and EP-A 132,736 reveal processes in which boron, gallium, aluminum, and iron silicate zeolites are used for the preparation of amines from olefins and reference is made to the possibility of doping these zeolites with alkali metals, alkaline earth metals, and transition metals. Use is preferably made of metal-modified or halogen-modified β-zeolites.

All processes for the synthesis of amines from olefins over these catalysts are distinguished by a low amine yield or low space-time yield, or lead to rapid deactivation of the catalysts.

It is thus at object of the present invention to overcome these drawbacks.

Accordingly, we have found a novel and improved process for the preparation of amines of the general formula I

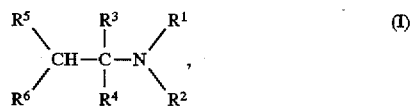

in which $R^1$, $R^2$, $R^3$, $R^4$, $R^5$, $R^6$ denote hydrogen, $C_1$-$C_{20}$ alkyl, $C_2$-$C_{20}$ alkenyl, $C_2$-$C_{20}$ alkynyl, $C_3$-$C_{20}$ cycloalkyl, $C_4$-$C_{20}$ alkylcycloalkyl, $C_4$-$C_{20}$ cycloalkylalkyl, aryl, $C_7$-$C_{20}$ alkylaryl, or $C_7$-$C_{20}$ aralkyl, $R^1$ and $R^2$ together denote a saturated or unsaturated $C_3$-$C_9$ alkylene dichain and $R^3$ or $R^5$ denotes $C_{21}$-$C_{200}$ alkyl, $C_{21}$-$C_{200}$ alkenyl or they together form a $C_2$-$C_{12}$ alkylene dichain, by the reaction of olefins of the general formula II

in which $R^3$, $R^4$, $R^5$, and $R^6$ have the above meanings, with ammonia or primary or secondary amines of the general formula III

in which $R^1$ and $R^2$ have the above meanings, at temperatures ranging from 200° to 350° C. and pressures ranging from 100 to 300 bar in the presence of a heterogeneous catalyst, wherein the heterogeneous catalyst used is a zeolite of the type SSZ-37.

The process of the invention can be carried out as follows:

The olefin II and ammonia or the primary or secondary amine III can be caused to react at temperatures ranging from 200° to 350° C., preferably from 220° to 330° C. and more preferably from 230° to 320° C. and pressures of from 100 to 300 bar, preferably from 120 to 300 bar and more preferably from 140 to 290 bar in the presence of zeolites of the type SSZ-37 acting as catalyst eg in an autoclave, and the amine obtained can preferably be separated and the unconverted starting materials recycled.

The present process is distinguished by a very good yield, high selectivity, and high space-time yield. In addition deactivation of the catalyst has been repressed.

The process of the invention is characterized in that even at a low excess of ammonia or amine a high selectivity toward the desired reaction product is achieved and dimerization and/or oligomerization of the olefin used is avoided.

One embodiment of this process consists in mixing ammonia and/or amines III together with the olefin II in a molar ratio of from 1:1 to 5:1, feeding the mixture to a fixed bed reactor, and causing it to react under a pressure of from 100 to 300 bar and at a temperature of from 200° to 350° C. in the gas phase or in a supercritical state.

The desired product can be obtained from the effluent by known methods, eg distillation or extraction, and worked up to the desired degree of purity if necessary by means of further separations. The unconverted starting materials are preferably usually recycled to the reactor.

Mono-unsaturated or poly-unsaturated olefins II, particularly those containing from 2 to 10 carbon atoms or mixtures thereof and polyolefins can be used as starting materials. Due to their low degree of basic polymerization proneness monoolefins are more suitable than diolefins and polyolefins, although these can be caused to react at similar selectivity by using higher excesses of ammonia or amine. The point of equilibrium and thus the degree of conversion to the desired amine is very much governed by the reaction pressure used. High pressure favors formation of the addition product, although a pressure range having an upper limit of 300 bar is generally the optimum for technical and economical reasons. The selectivity of the reaction is to a great extent influenced by the temperature—in addition to factors such as excess of ammonia/amine and catalyst. Although the reaction velocity of the addition reaction increases steeply with increasing temperature, competitive cracking and recombining reactions of the olefin are simultaneously promoted. In addition a temperature increase is not advantageous from a thermodynamic point of view. The optimum temperature as regards conversion and selectivity is dependent on the nature of the olefin, the amine used and the catalyst and is usually in a range extending from 200° to 350° C.

Suitable catalysts for the amination of olefins are zeolites of the type SSZ-37, which are described in, eg, U.S. Pat. No. 5,254,514 or WO-A 94/00233.

The zeolites SSZ-37 of the invention can be shaped as such, or alternatively mixed with a binding agent in a percentage ratio, by weight, of from 98:2 to 40:60 to form extrudates or pellets. Suitable binding agents are various aluminum oxides, preferably boehmite, amorphous aluminum silicates having a $SiO_2/Al_2O_3$ ratio of from 25:75 to 95:5, silicon dioxide, preferably microdispersed $SiO_2$, mixtures of microdispersed $SiO_2$ and microdispersed $Al_2O_3$, microdispersed $TiO_2$, and also clays. Following shaping, the extrudates or molded articles are advantageously dried at 110° C. over a period of 16 h and calcined at from 200° to 500° C. over a period of from 2 h to 16 h, which calcination may be carried out in situ in the amination reactor, if desired.

In order to increase the selectivity, the on-stream time and the number of the possible regenerations various modifications can be performed on the zeolite catalysts SSZ-37 of the invention.

One modification of the catalysts consists in effecting ion exchange on or doping the unshaped or shaped zeolites with alkali metals such as Na and K, alkaline earth metals such as Ca and Mg, earth metals such as Tl, transition metals such as Ti, Zr, Mn, Fe, Mo, Cu, Zn, Cr, noble metals, and/or rare earth metals such as La, Ce, or Y.

One advantageous embodiment consists in placing in a flow tube the shaped zeolites SSZ-37 of the invention and passing over eg a halide, an acetate, an oxalate, a citrate, or a nitrate of the aforementioned metals in dissolved form at 20° to 100° C. Such ion exchange can be performed on eg the hydrogen, ammonium, and alkali metal forms of the zeolites SSZ-37 of the invention.

Another possibility of applying metal to the zeolites SSZ-37 of the invention consists in impregnating the material with, eg, a halide, an acetate, an oxalate, a citrate, a nitrate, or an oxide of the aforementioned metals in aqueous or alcoholic solution.

Both ion exchange and an impregnation step can be followed by a drying step and optionally by another calcination step. In the case of metal-doped zeolites of the type SSZ-37 post-treatment with hydrogen and/or steam can be favorable.

Another possibility for modification consists in subjecting the zeolites SSZ-37 of the invention—shaped or unshaped—to treatment with acids, such as hydrochloric acid (HCl), hydrofluoric acid (HF), sulfuric acid ($H_2SO_4$), oxalic acid ($HO_2C-CO_2H$), phosphoric acid ($H_3PO_4$), or mixtures thereof.

A particular embodiment consists in refluxing the zeolites SSZ-37 of the invention prior to shaping with one of the said acids in a strength of from 0.001N to 2N and preferably from 0.05 to 0.5N over a period of from 1 to 100 hours. Following filtering and washing drying is usually carried out at 100° to 160° C. and calcination at 200° to 600° C. Another special embodiment resides in the acid treatment of the zeolites SSZ-37 of the invention following shaping thereof with binding agent. In this case the zeolite of the invention is usually treated with a from 3 to 25% strength, particularly a from 12 to 20% strength acid for from 1 to 3 hours at a temperature between 60° and 80° C., then washed, dried at 100° to 160° C., and calcined at 200° to 600° C. Here again, said calcination may be carried out in situ in the amination reactor, if desired.

Another possibility for modification is provided by an exchange with ammonium salts, eg, $NH_4Cl$ or mono-, di-, or poly-amines. In this case the zeolite shaped with binding agent is usually exchanged with from 10 to 25% strength, preferably 20% strength $NH_4Cl$ solution at 60° to 80° C. over a period of 2 h continuously in 1:15 zeolite/ammonium chloride solution, by weight, and then dried at 100° to 120° C.

Yet another way of modifying the zeolites of the invention involves dealumination, in which case some of the aluminum atoms are replaced by silicon or the zeolites are subjected to, say, hydrothermal treatment to reduce their aluminum content. Such hydrothermal treatment is advantageously followed by extraction with acids or complexing agents in order to remove any non-lattice aluminum formed. Replacement of aluminum by silicon may be affected, for example, by treatment with $(NH_4)_2SiF_6$ or $SiCl_4$. Examples of dealuminations of Y-type zeolites are given in Corma et al., Stud. Surf. Sci. Catal. 37 (1987), pp. 495–503.

The catalysts can be used for the amination of the olefins in the form of extrudates having diameters of, eg, from 1 to 4 mm or pellets having a diameter of, say, from 3 to 5 mm.

A fluid bed material having a particle size of from 0.1 to 0.8 mm can be obtained from the catalyst shaped, eg, in the form of extrudates, by milling and screening.

The substituents $R^1$, $R^2$, $R^3$, $R^4$, $R^5$, and $R^6$ in the compounds I, II and III have the following meanings:

$R^1$, $R^2$, $R^3$, $R^4$, $R^5$, $R^6$ hydrogen, $C_1-C_{20}$ alkyl, preferably $C_1-C_{12}$ alkyl and more preferably $C_1-C_8$ alkyl such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl, and isooctyl, $C_2-C_{20}$ alkenyl, preferably $C_2-C_{12}$ alkenyl and more preferably $C_2-C_8$ alkenyl such as vinyl and allyl, $C_2-C_{20}$ alkynyl, preferably $C_2-C_8$ alkynyl, particularly $C_2H$ and propargyl, $C_3-C_{20}$ cycloalkyl, preferably $C_3-C_{12}$ cycloalkyl and more preferably $C_5-C_8$ cycloalkyl such as cyclopentyl, cyclohexyl, cycloheptyl, and cyclooctyl, $C_4-C_{20}$ alkylcycloalkyl, preferably $C_4-C_{12}$ alkylcycloalkyl and more preferably $C_5-C_{10}$ alkylcycloalkyl, $C_4-C_{20}$ cycloalkylalkyl, preferably $C_4-C_{12}$ cycloalkylalkyl and more preferably $C_5-C_{10}$ cycloalkylalkyl, aryl such as phenyl, 1-naphthyl, and 2-naphthyl, preferably phenyl, $C_7-C_{20}$ alkylaryl, preferably $C_7-C_{16}$ alkylaryl, preferably $C_7-C_{12}$ alkylphenyl such as 2-methylphenyl, 3-methylphenyl, 4-methylphenyl, 2-ethylphenyl, 3-ethylphenyl, and 4-ethylphenyl, $C_7-C_{20}$ aralkyl, preferably $C_7-C_{16}$ aralkyl, preferably $C_7-C_{12}$ phenalkyl such as phenylmethyl, 1-phenylethyl, 2-phenylethyl, $R^1$ and $R^2$ together form a saturated or unsaturated $C_3-C_9$ alkylene dichain, preferably $-(CH_2)_4-$, $-(CH_2)_5-$, $-(CH_2)_7-$ and $-CH=CH-CH=CH-$, $R^3$ or $R^5$ $C_{21}-C_{200}$ alkyl, preferably $C_{40}-C_{200}$ alkyl such as polybutyl, polyisobutyl, polypropyl, polyisopropyl, and polyethyl and more preferably polybutyl and polyisobutyl, $C_{21}-C_{200}$ alkenyl, preferably $C_{40}-C_{200}$ alkenyl and more preferably $C_{70}-C_{170}$ alkenyl, $R^3$ and $R^5$ together form a $C_2-C_{12}$ alkylene dichain, preferably a $C_3-C_8$ alkylene dichain and more preferably $(CH_2)_3-$, $-(CH_2)_4-$, $-(CH_2)_5-$, $-(CH_2)_6-$ and $-(CH_2)_7-$, preferably $(CH_2)_3$ and $CH_2)_4-$.

EXAMPLES

Catalyst synthesis 60 g of SSZ-37 were admixed with 40 g of boehmite and 2 g of formic acid, compacted in a kneader, and kneaded over a period of 45 minutes with the addition of water (105 ml). 2 mm extrudates were produced in an extruder using a molding pressure of 40 bar, dried at 120° C. over a period of 16 h and then calcined at 500° C. over a period of 16 h.

Amination examples

The experiments were carried out in a tubular reactor (internal diameter 6 mm) under isothermal conditions at a temperature of from 260° to 300° C. and a pressure of 280 bar using a mixture of isobutene and ammonia in a molar ratio of 1:1.5. The reaction products were analysed by gas chromatography.

The results are listed in Table 1.

TABLE 1 tert-butylamine ($NH_3$ : $C_4H_8$ = 1.5)

| Pressure [bar] | Temperature [°C.] | tert-butylamine yield [wt %] | | | Weight per liter [kg/L] |
|---|---|---|---|---|---|
| | | WHSV 0.7 [g/g · h] | WHSV 1.5 [g/g · h] | WHSV 3 [g/g · h] | |
| 280 | 260 | 17.6 | | | 0.47 |
| 280 | 270 | 20.2 | 17.0 | 13.0 | 0.47 |
| 280 | 280 | 17.7 | 16.5 | 14.0 | 0.47 |
| 280 | 300 | | | 11.5 | 0.47 |

We claim:

1. A process for the preparation of an amine of the general formula I

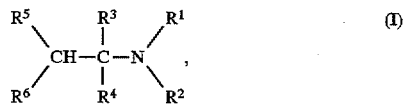

in which $R^1$, $R^2$, $R^3$, $R^4$, $R^5$, $R^6$ denote hydrogen, $C_1$–$C_{20}$ alkyl, $C_2$–$C_{20}$ alkenyl, $C_2$–$C_{20}$ alkynyl, $C_3$–$C_{20}$ cycloalkyl, $C_4$–$C_{20}$ alkylcycloalkyl, $C_4$–$C_{20}$ cycloalkylalkyl, aryl, $C_7$–$C_{20}$ alkylaryl, or $C_7$–$C_{20}$ aralkyl, $R^1$ and $R^2$ additionally together denote a saturated or unsaturated $C_3$–$C_9$ alkylene dichain and $R^3$ or $R^5$ additionally denotes $C_{21}$–$C_{200}$ alkyl, $C_{21}$–$C_{200}$ alkenyl or they together form a $C_2$–$C_{12}$ alkylene dichain, by the reaction of an olefin of the general formula II

in which $R^3$, $R^4$, $R^5$, and $R^6$ have the above meanings, with ammonia or a primary or secondary amine of the general formula III

in which $R^1$ and $R^2$ have the above meanings, at temperatures ranging from 200° to 350° C. and pressures ranging from 100 to 300 bar in the presence of a heterogeneous catalyst, wherein the heterogeneous catalyst used is a zeolite of the type SSZ-37.

2. A process for the preparation of an amine I as defined in claim 1, wherein the amine I formed is separated and the unconverted starting materials II and III are recycled.

3. A process for the preparation of an amine as defined in claim 1, wherein the olefin II used is isobutene, diisobutene, cyclopentene, cyclohexene, or polyisobutene.

4. A process for the preparation of an amine as defined in claim 1, wherein the heterogeneous catalyst used is an SSZ 37 zeolite in the H form.

5. A process for the preparation of an amine as defined in claim 1, wherein the heterogeneous catalyst used is an SSZ 37 zeolite which has been treated with an acid, particularly one selected from the group consisting of hydrochloric acid, hydrofluoric acid, sulfuric acid, oxalic acid, phosphoric acid and mixtures thereof.

6. A process for the preparation of an amine as defined in claim 1, wherein the heterogeneous catalyst used is an SSZ 37 zeolite which has been doped with one or more transition metals.

7. A process for the preparation of an amine as defined in claim 1, wherein the heterogeneous catalyst used is an SSZ 37 zeolite which has been doped with one or more rare earth elements.

8. A process for the preparation of an amine as defined in claim 1, wherein the heterogeneous catalyst used is an SSZ 37 zeolite in the ammonium form.

9. A process for the preparation of amines as defined in claim 1, wherein the heterogeneous catalyst used is an SSZ 37 zeolite which has been doped with one or more elements selected from the group consisting of the alkali metals, alkaline earth metals, or earth metals.

10. A process for the preparation of an amine as defined claim 1, wherein the heterogeneous catalyst used is an SSZ 37 zeolite which has been shaped with a binding agent and calcined at temperatures ranging from 200° to 600° C.

11. A process for the preparation of an amine as defined in claim 1, wherein the heterogeneous catalyst used is a dealuminated SSZ 37 zeolite.

* * * * *